United States Patent
Boekstegers

(10) Patent No.: US 6,458,323 B1
(45) Date of Patent: Oct. 1, 2002

(54) METHOD AND DEVICE FOR THE VASCULAR PRESSURE-CONTROLLED SELECTIVE PERFUSION OF FLUIDS THROUGH BLOOD VESSELS

(76) Inventor: Peter Boekstegers, Prälatenstrasse 15D, D-86811 Diessen (DE)

( * ) Notice: Subject to any disclaimer, the term of this patent is extended or adjusted under 35 U.S.C. 154(b) by 66 days.

(21) Appl. No.: 08/945,488

(22) PCT Filed: Apr. 19, 1996

(86) PCT No.: PCT/EP96/01657
§ 371 (c)(1),
(2), (4) Date: Feb. 10, 1998

(87) PCT Pub. No.: WO96/32972
PCT Pub. Date: Oct. 24, 1996

(30) Foreign Application Priority Data

Apr. 20, 1995 (DE) .......................... 195 14 638

(51) Int. Cl.⁷ .......................... A61M 1/36; A61M 37/00; A61N 1/362; A61B 5/02
(52) U.S. Cl. .......................... 422/44; 604/4.01; 604/6.11; 604/28; 600/17; 600/504
(58) Field of Search .......................... 624/4–6; 128/898, 128/DIG. 5, DIG. 20; 604/4.01, 5.01, 6.01, 6.09, 6.1, 6.11, 6.14, 19, 30, 28, 65–67, 93.01, 131, 151, 31; 422/44–45, 82.13; 600/301, 334, 363, 366, 368, 500–502, 504–505, 437–439, 454, 459–468, 485–486, 493, 16–18; 417/1, 63, 212, 279, 282, 321, 378, 383, 428, 253; 606/191, 194

(56) References Cited

U.S. PATENT DOCUMENTS

| | | | |
|---|---|---|---|
| 4,456,000 A | * | 6/1984 | Schjeldahl et al. |
| 4,459,977 A | | 7/1984 | Pizon et al. |
| 4,648,384 A | * | 3/1987 | Schmukler |
| 4,689,041 A | * | 8/1987 | Corday et al. |
| 4,804,358 A | | 2/1989 | Karcher et al. |
| 4,865,581 A | | 9/1989 | Lundquist et al. |
| 5,011,468 A | | 4/1991 | Lundquist et al. |
| 5,024,668 A | * | 6/1991 | Peters et al. ................. 606/194 |
| 5,057,120 A | | 10/1991 | Farcot |

FOREIGN PATENT DOCUMENTS

| | | |
|---|---|---|
| DE | 4003425 A1 | 8/1991 |
| DE | 4201259 C2 | 7/1993 |
| DE | 4310378 A1 | 10/1994 |
| EP | 0297723 B1 | 1/1989 |
| EP | 0357338 | 3/1990 |
| EP | 0364799 A2 | 4/1990 |
| EP | 0445079 A2 | 9/1991 |
| WO | WO 9523620 | 9/1995 |

OTHER PUBLICATIONS

"Selective ECG synchronised suction and retroinfusion of coronary veins: first results of studies in acute mycardial ischemia in dogs", Boekstegers et al. Cardiovascular Research, Jun. 1990.*

P. Boekstegers et al., "Preservation of Regional Myocardial Function . . . " JACC, vol. 23, pp. 459–469 (1994).

* cited by examiner

Primary Examiner—Angela D. Sykes
Assistant Examiner—P. M. Bianco
(74) Attorney, Agent, or Firm—McDonnell Boehnen Hulbert & Berghoff

(57) ABSTRACT

A method for selective perfusion of fluids through blood vessels is controlled by the pressure in the blood vessels. A tubing line open at the proximal end for the perfusion of fluids through a tissue region is introduced into a patient's blood vessel in which perfusion is to be performed. The vessel is sealed off from the line in the area of its proximal end, and fluid is pumped into the vessel. The method is characterized in that a specific set value for the internal pressure of the vessel is measured, and the perfused flow of fluid is regulated during pumping in such a way that the set value for the internal pressure of the vessel is kept as closely as possible.

26 Claims, 4 Drawing Sheets

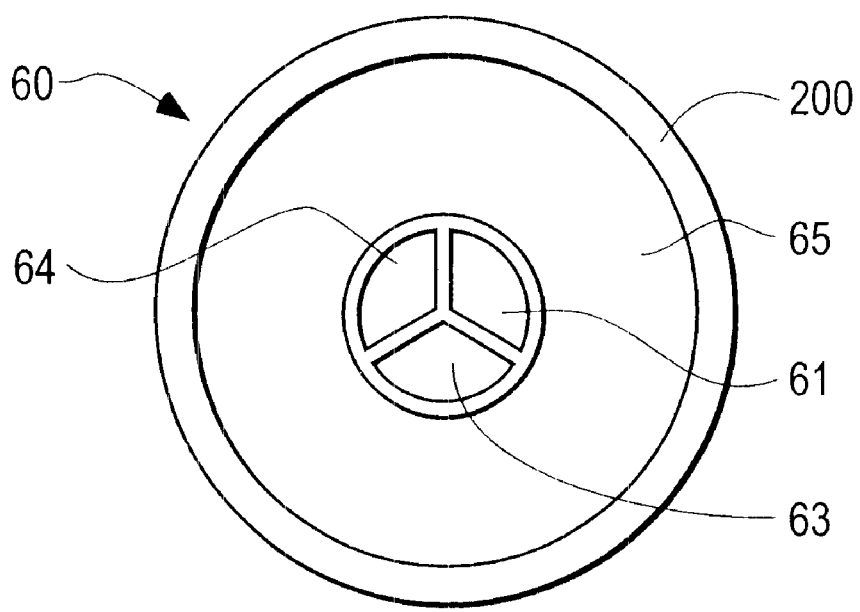

METHOD AND DEVICE FOR THE VASCULAR PRESSURE-CONTROLLED SELECTIVE PERFUSION OF FLUIDS THROUGH BLOOD VESSELS

The present invention relates to a method and a device for the selective perfusion of fluids through blood vessels, controlled by the pressure in the blood vessels. In particular, the present invention relates, on the one hand, to the suction of a fluid out of, and the retroinfusion of a fluid into, veins, in particular coronary veins, controlled by the pressure in the veins, and, on the other hand, to the perfusion of fluids through arteries, in particular coronary arteries, controlled by the pressure in the arteries.

The nutritive perfusion of coronary arteries and retroinfusion of blood into coronary veins becoming increasingly important, especially in the area of myocardial protection during, short-term coronary artery closure in the context of a cardiac intervention. A typical intervention of this kind is, for example, the balloon dilation of a coronary artery which has become narrowed as a result of arteriosclerosis. In this method, which is also known as percutaneous transluminal coronary angioplasty (PTCA), a balloon catheter is guided, with radiographic monitoring, into the area of the stenosis of the coronary artery, and the arteriosclerotic plaque is compressed by inflating the balloon situated at the end of the catheter. During the dilation of the balloon, there is no supply of oxygenated blood to the tissue in the downstream area of the artery In most cases this does not pose any problem, as long as the dilation lasts only a short time. However, in the case of dilations of more than just 30 seconds' duration, functional changes in the ischaemic area of the myocardium can be detected, for example as ST-changes on the electrocardiogram, as a reduction in regional wall movement by echo cardiography, or else subjectively by the patient as angina pectoris symptoms. In addition, the risk of complications in angioplasty is higher for certain groups of patients, for instance in elderly patients, in cases of unstable angina, in cases of a decreased left-ventricular ejection fraction, or in cases of dilation of a vessel which supplies more than 40% of the left ventricle.

Corresponding problems in protecting against myocardial ischaemia also arise in other operations for coronary vascularization, such as, for example, in atherectomy, coronary endoprostheses and laser applications.

It is known to effect short-term ischaemic protection by machine perfusion of an artery supplying the affected region of the myocardium, for instance the actual artery which is to be dilated, either with arterial blood, which has been taken from the patient, at another site or with other nutritive fluids. In doing so, however, there is a danger of overperfusion of the myocardial tissue, which is particularly the case if the outflow of the perfused fluid from the affected tissue is impeded or completely blocked. In such cases, this may lead to haemorrhagic tissue infarcts in the affected region of the myocardium.

A further possibility for short-term protection against ischaemia, which has been used for some time now in cases where complications are anticipated, is the retroinfusion of arterial blood into a vein of the area of myocardial ischaemia concerned. The arterial blood is in this case pumped through the corresponding vein into the nutritive capillaries of the ischaemic area and so supplies the myocardium in this region with oxygen and substrates.

Devices for retroinfusion of coronary veins have been known for some years. Thus, European Patent Specification EP-B-0 297 723 describes a retroinfusion unit with which arterial blood is taken, for example, from the femoral artery of the patient and is conveyed to a coronary vein of the ischaemic area via a pump system and an inflatable balloon catheter. The pumping of arterial blood into the coronary vein is in this case synchronized with the R wave of the patient's electrocardiogram, so that the pumping interval is adapted to the patient's cardiac cycle. The pumping interval is in this case predefined and begins at 45% of the R—R interval and ends at 950% of the R—R interval. The infused blood flow is in this case essentially constant during the pumping interval. As long as pumping is being carried out, the balloon of the balloon catheter is inflated and blocks the vein, thus ensuring that arterial blood is effectively transported into the ischaemic area during the diastole. The pumping procedure ends at the end of the diastole and the balloon is emptied, so that the flow in the vein is no longer blocked at this point. During the succeeding systole, venous blood can flow off through the vein.

With the device described in EP 0 297 723, the basal metabolism of the ischaemic area can be satisfactorily maintained during a short-term cardiac intervention. It was furthermore observed that the size of myocardial infarction following a coronary artery closure was significantly reduced. However, it was also found that the local myocardial function is not sufficiently maintained. For example, the local myocardial function breaks down completely in the absence of arterial collateralization of the ischaemic area. One cause of this is to be seen primarily in the incomplete exchange of arterial and venous blood in the retroinfused vein system in the course of a cardiac cycle.

In order to improve this blood exchange, with the aim of better maintaining the myocardial function in the ischaemic area, Boekstegers et al. have recently proposed, in *Cardiovascular Research* 1990, 24: 456–464, and in *JACC* 1994, 23: 459–469, a system for retroinfusion of coronary veins in which, instead of venous blood flowing off passively during the systole, an active suction through the retroinfusion catheter takes place. For this purpose, the balloon of the catheter also remains inflated in the suction interval and blocks the vein during the systole too. When a device of this kind was used in the animal model, improved maintenance of the myocardial function during coronary artery closure was demonstrated.

However, with regard to clinical application in a patient, the system still has disadvantages.

Thus, in this device, in the same way as in the device in EP 0 297 723, although the pumping volume per pump stroke can be adjusted, the flow of the retroinfused blood cannot, however, be influenced during a pumping interval. It has, however, been shown that the intravenous pressure is subject to considerable fluctuations in the course of one pumping interval as a result of this. Even if the intravenous pressure is recorded, although a desired mean pressure can be set in the course of several pumping intervals, the considerable fluctuations in pressure within one pumping interval cannot be eliminated.

There are, however, some problems associated with these considerable changes in the coronary vein pressure. Thus, it has been found that with a low retroinfusion flow, i.e. at a low venous pressure, an adequate supply of oxygen to the myocardium is not guaranteed, with the result that the myocardial function in the ischaemic area cannot be satisfactorily maintained. With a high infusion flow, i.e. at too high a coronary vein pressure, there is a danger, however, of overperfusion occurring, which does not improve the retrograde nutritive capillary filling, but only impedes the contraction of the myocardium and leads to an ineffective outflow of the arterial blood into the systemic circulation. In the case of retro-infusion at too high a coronary vein pressure, there is also a danger of irreversible damage to the vessel wall.

The object of the present invention is therefore to make available a method and a device for the perfusion of blood vessels, in particular coronary vessels, in which method the perfusion is performed at a vascular pressure which is optimum for nutritive capillary filling, and where this set pressure is maintained as constant as possible during pumping. The method according to the invention and the device according to the invention are in this case intended to make it possible to extend the application possibilities of vascular perfusion, in particular arterial perfusion and venous retroinfusion, beyond the hitherto short-term myocardial protection.

According to the invention, a method is provided for the selective perfusion of fluids through blood vessels, controlled by the pressure in the blood vessels, in which method a tubing line open at the proximal end for the perfusion of fluids through a tissue region is introduced into a patient's blood vessel in which perfusion is to be performed, the vessel is sealed off from the line in the area of its proximal end, and the fluid is pumped into the vessel, the method being characterized in that a specific set value for the internal pressure of the vessel is predefined, the internal pressure of the vessel is measured, and the perfused flow of fluid is regulated during pumping in such a way that the set value for the internal pressure of the vessel is kept as closely as possible.

According to the invention, and in contrast to the known perfusion methods, the flow of fluid during the pumping of fluid is no longer determined only by the pumping volume per pump stroke, with the effect that the volume flow pattern during the pumping phase cannot be influenced, and instead it is regulated in accordance with the measured vascular pressure. General methods known in measurement and control technology may be used as the regulating method, the actual blood pressure in the vessel being utilized as a control variable, and the flow of fluid actually infused being utilized as an adjustable variable. The control function here can take account of the typical elastic properties of a blood vessel on the basis of predefined parameters and can adapt these parameters, if appropriate by evaluating the dynamics of the system, to the circumstances pertaining to the specific individual case. In particular, the control system will extrapolate the future pressure pattern on the basis of the current pressure pattern and will adapt the flow of fluid at the right time. The control system is set up in such a way that the response time is less than 25 milliseconds.

Advantageously, the fluid is pumped periodically into the vessel at intervals, the pumping intervals being synchronized with the patient's heartbeat.

However, it is also possible, particularly in the case of perfusion of arteries, to pump the fluid into the vessel continuously.

The set value which is to be defined for the vascular pressure is an individual value which will depend on the particular patient, the vessel in which infusion is to be performed, and the specific site of the perfusion in the vessel.

The set value for the pressure inside the artery is advantageously chosen such that the nutritive perfusion is maintained.

If nutritive fluid is retroinfused into a vein, then the fluid is periodically infused via the tubing line into the vein and blood is periodically suctioned from the vein via the tubing line. The pumping and suction intervals are preferably synchronized with the patient's heartbeat.

According to the invention, it has surprisingly been found that it is possible to individually fix the desired set value of the venous pressure for the particular situation in a separate measurement before the start of the actual retroinfusion. According to the invention, the set value for the pressure inside the vein is defined such that, with the vein sealed off, either the venous pressure is measured without retroinfusion, with venous blood flow present, or, if there is no blood flow, infusion is performed with the flow of fluid increasing at each pumping interval and in so doing the internal pressure of the vein is measured. It is found that the peak venous pressure does not increase in proportion to the increasing flow of fluid, but rather approaches a limit value (plateau pressure). It may be assumed that the maximum retrograde nutritive capillary filling is reached at this plateau pressure, and that with a higher flow of fluid there is only an ineffective outflow into the systemic circulation. According to the invention, it is therefore proposed to predefine this plateau pressure as the set value for the venous pressure during retro-infusion.

In the case of protection of the myocardium from ischaemia or of tissue protection in general, the infused or perfused fluid is preferably an oxygen carrier. The oxygen carrier used is preferably blood, in which case it is particularly advantageous to use the patient's own arterial blood, which is taken, for example, from the femoral artery and is conveyed to the vein in which retrofusion is to be performed via a pump, a blood filter for cleaning the blood and an air trap for freeing the blood of air bubbles, at a pressure of preferably about 2 bar via a flow control means. However, it is also possible to use a blood substitute, such as, for example, a fluorocarbon or perfluorocetyl bromide solution as oxygen carrier.

The fluid infused through the veins or perfused through the arteries of the patient may also, however, contain therapeutic or diagnostic active substances, such as, for example, anticoagulants, contrast media or beta-blockers.

If the vein in which retroinfusion is to be performed is, for example, a leg vein in which there is a thrombus, then it will be advantageous to supplement the fluid with means for dissolving this thrombus. In this way it is possible, for example, to apply high concentrations of a medicament locally, without the other physical functions being adversely affected by this.

According to one embodiment of the method according to the invention, venous blood or retroinfusate is actively suctioned between the pumping phases. This blood is led into a reservoir via a vacuum pump. In the case of short-term retroinfusion of a vein, the amount of blood which is suctioned in this way is relatively small. In the case of more prolonged retroinfusion, for example when protecting the myocardium from ischaemia during a prolonged coronary artery closure, it may be advantageous to defoam the blood, which has been suctioned in one suction-interval, and to free it of air bubbles and then return it to the patient via a vein. This effectively avoids the patient suffering a blood loss limiting the duration of application of the method according to the invention.

According to the invention, a device is also made available for the selective perfusion of a fluid through blood vessels, controlled by the pressure in the blood vessels, which device is particularly suitable for carrying out the above-described method. The device has a tubing line which can be introduced into a patient's blood vessel, is open at the proximal end and can be charged with a fluid under pressure which is to be pumped into the blood vessel, the proximal end being provided with an enlargeable sealing means with which the vessel can be sealed off from the line. Means for measuring the internal pressure of the vessel and regulating means are additionally provided, with the aid of which a control unit regulates the perfused flow of fluid so that a defined pressure inside the blood vessel is kept as constant as possible during pumping.

If a vein is retroinfused using the device according to the invention, then the line is advantageously connected to a suction device for blood from the patient's vein, and the control unit receives signals from the patient's heartbeat and defines pumping and suction intervals which are synchronized with the patient's heart cycle.

According to one preferred embodiment, the admission and suction line is a multi-lumen catheter. In an embodiment suitable for retroinfusion, this is an at least four-lumen vein catheter, including an admission line for the fluid, a suction line for the suctioned blood, a measurement line for determining the internal pressure of the vein, and a control line for the enlargeable sealing means. For arterial perfusion, an at least three-lumen artery catheter is advantageously used, including an admission line for the fluid, a measurement line for determining the internal pressure of the artery, and a control line for the enlargeable sealing means.

The sealing means is advantageously a pressure-controlled, inflatable balloon, so that a balloon catheter can be used as the catheter. The balloon is then preferably situated at the end of the catheter that is introduced into the blood vessel. The measurement line for determining the internal pressure of the blood vessel communicates at one end with the inside of the vessel and has a pressure sensor at its other end. However, it is also possible to arrange a pressure sensor at the proximal end of the line, which pressure sensor is connected to the control unit by a fine cable which can be guided, for example, through the control line for the inflatable balloon. In this case, a three-lumen catheter would be sufficient, for example. Moreover, the admission line and the suction line can be designed as one line at the proximal end of the catheter, which one line is then connected to the supply reservoir or the suction reservoir via a switchable 3-way valve.

Depending on the task in hand, it is also possible to provide a catheter which has additional lines, for example a glass fibre cable for laser applications or video recordings.

In a preferred embodiment, the regulating means for the perfused flow of fluid comprise a flow regulator which is advantageously designed such that the admission line has an elastically yielding tubing in the area of this flow regulator, the flow regulator comprising a clamping member which is driven by-an electric motor and which presses the elastic tubing together to a greater or lesser extent and so controls the retroinfused flow of the fluid into the blood vessel. The electric motor is preferably a stepping motor controlled by the control unit, an eccentric arranged on the axle of the stepping motor activating the clamping member, and the clamping member being preferably designed as a crossbar oriented essentially perpendicular to the fluid admission line. The admission line in this case lies on a rigid support.

The distal end of the admission line is preferably connected to a fluid reservoir which is under pressure and which advantageously has a pressure sensor for monitoring the pressure in the reservoir. It is from this reservoir that the admission line is supplied with the fluid to be infused.

In a further embodiment, the blood taken from an artery of the patient is fed to this reservoir via a roller pump. The suction device for the venous blood preferably has a vacuum pump and a reservoir for the suctioned blood. If the suctioned blood is intended to be returned to the patient, then this blood will preferably be led into a reservoir from which it can thereafter be conveyed via a roller pump, an air trap and a defoaming device to a vein of the patient.

The synchronization with the patient's heart cycle is preferably effected via the lead of an electrocardiogram (ECG), the R wave advantageously being used as trigger signal. The pumping cycle advantageously begins between 15 and 50% of the R—R interval and ends at the start of the following R wave. It is also conceivable, however, to vary the pumping phase within wide limits, so that, where appropriate, it can even last beyond the following R wave of the ECG. A fixed ratio of pumping phases to heart cycles is normally chosen, for example 1:1, 1:2, 1:3, etc. Suction is preferably always performed between the individual pumping phases. It may also be advantageous, however, to provide phases in which neither pumping nor suction is carried out.

The method according to the invention and the device for controlling the coronary vein pressure during an individual pumping interval has numerous advantages over the known retroinfusion devices:

In the case of arterial perfusion, for example in antegrade catheter perfusion of a coronary artery, the desired perfusion pressure can be maintained both with the balloon blocked and also with it unblocked at the pressure can be regulated within certain limits of tolerance in a narrow range about the optimum perfusion pressure and can be kept substantially constant. In particular, however, it is possible to avoid overperfusion and the associated haemorrhagic tissue infarcts even when the outflow of the perfusate in the tissue is disrupted. The reason for this is that after an inadmissible increase in the arterial pressure, further perfusion of fluid only takes place again after the pressure has dropped once more below the predefined set value.

In retroinfusion, by preventing a substantial increase in the coronary vein pressure above a preset limit value in the course of a pumping interval, it is possible to prevent potentially dangerous peak pressure increases developing, which could cause damage to the vessel wall and, in extreme cases, rupture of the vessel.

The diastolic venous/arterial pressure gradient, which can be adjusted constantly using the device according to the invention, permits extremely effective retroinfusion since, on the one hand, the optimum pressure gradient for a nutritive circulation is provided, and, on the other hand, overperfusion is avoided.

Since the individually differing coronary vein pressure at which there is an increased outflow of retroinfused arterial blood into the systemic circulation can be determined by means of the plateau pressure in coronary vein occlusion even before interruption of the antegrade perfusion, the invention permits adjustment of the optimum coronary vein pressure range for each patient.

Above all, however, both the basal metabolism and the regional myocardial function in the ischaeinic area are markedly improved compared to the known method. The efficiency of the myocardial protection is markedly increased especially in patients with poor arterial collateralization. Damage to the retroinfused veins can to all intents and purposes be ruled out using the method according to the invention. Initial clinical tests suggest that the risk of complications in angioplasty procedures can be reduced.

However, the method according to the invention and the device according to the invention for the selective perfusion of blood vessels, controlled by the pressure in the blood vessels, is not limited to applications in short-term protection against ischaemia protection. In addition to the latter, more prolonged applications of the method are possible, for example, in complications with persistent closure of the coronary artery, as a stop-gap measure until surgical emergency bypass. This more prolonged protection against ischaemia is made possible in the first instance by the high degree of efficiency of supply to the tissues with the method according to the invention. In particular, when the suctioned venous blood, cleaned and defoamed, is reinfused into a vein of the patient, a more prolonged application. of the retroinfusion method according to the invention is also possible while maintaining the functional metabolism.

A further area of application lies in the identification of chronic, but reversible, regional left-ventricular dysfunction, also referred to as hibernating myocardium. Here, the method according to the invention, as a supplement to nuclear medicine techniques and NMR techniques, may permit determination of the myocardial metabolism, which permits differentiation of the necrotic or scarred myocardial tissue from still potentially metabolically active myocardial cells. In this case it is possible, for example in order to confirm the possible success of a bypass operation, to establish by means of retrograde perfusion. whether and to what extent the myocardial function can be restored by improving the nutritive perfusion.

A further possible area of application of the invention at present is the perfusion or reinfusion of cells which have been genetically treated in vitro, into the bodies of patients.

A preferred embodiment of the invention is explained in greater detail hereinafter with reference to the attached drawing. The illustrative embodiment concerns the case of retroinfusion of veins, but it can also be applied in principle to the perfusion of arteries. The essential difference in the perfusion of arteries is that blood is not suctioned and, accordingly, a three-lumen catheter can also be used.

In the drawing:

FIG. 3A is a cross-section of a three-lumen catheter.

Figure 1:
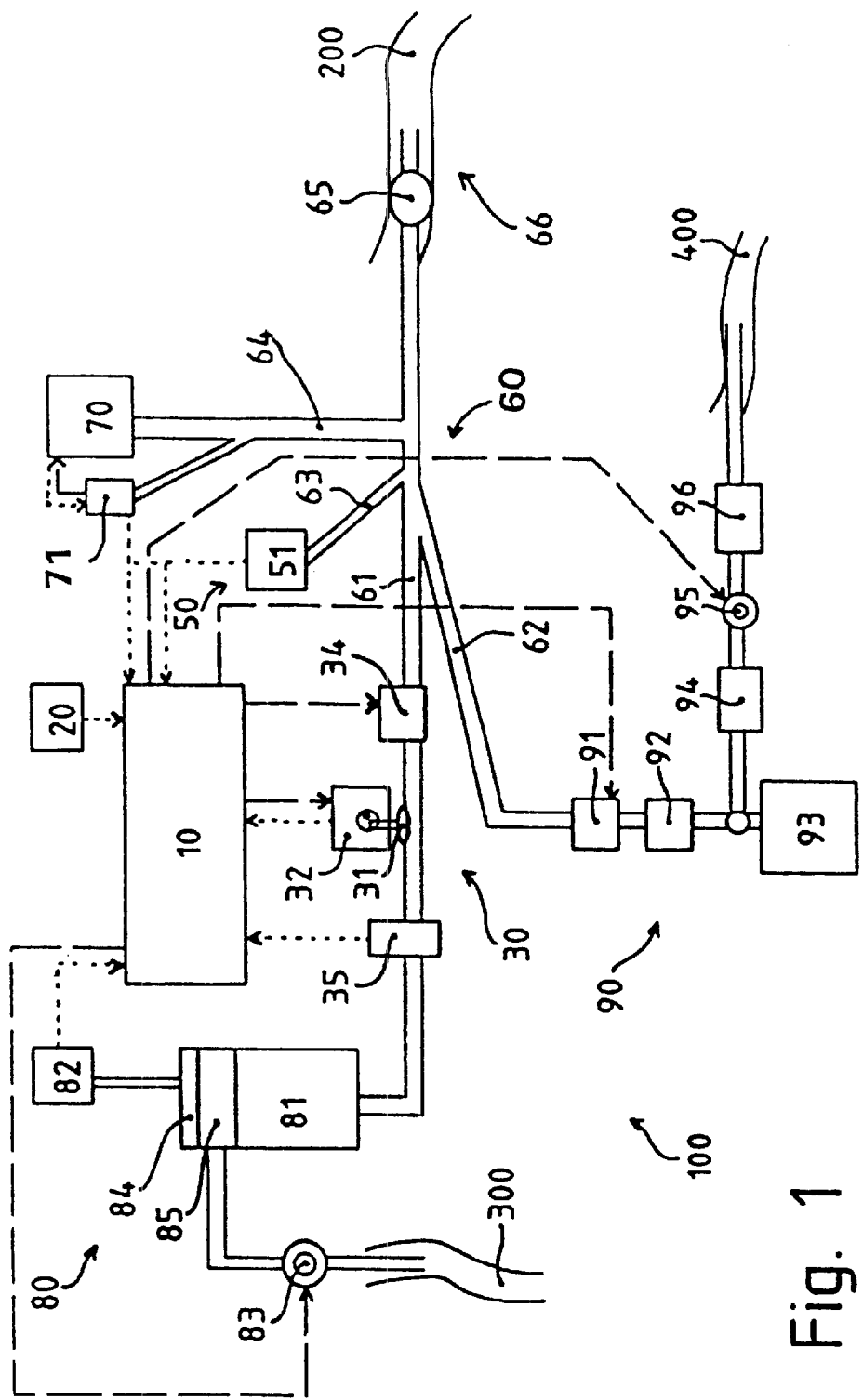
FIG. 1 shows a schematic representation of a device according to the invention for the selective suction and retroinfusion of veins, controlled by the pressure in the veins.

FIG. 1 shows a preferred embodiment of the device 100 according to the invention for the selective suction and retroinfusion of veins, controlled by the pressure in the veins. The device has what in the present case is a four-lumen tubing line 60, which is introduced as retroinfusion catheter into the vein 200 (for example the AIV vein) in which infusion is to be performed. Provided at the proximal end of the tubing (vein side) there is a sealing means 65 which is advantageously an inflatable balloon which seals off the vein 200 from the line 60, but at the same time permits the passage of fluid from the tubing line into the vein, or vice versa. For this purpose, an admission line 61 in particular is provided through which fluid can be pumped into the vein 200. To do this, the admission line is connected at its distal end (at the opposite end from the vein end) to a fluid supply 80. The fluid supply 80 comprises a fluid reservoir 81 which is under pressure, the pressure in the reservoir being monitored by means of a pressure sensor 82. When the fluid to be retroinfused is the patient's own blood, the reservoir 81 can be connected via a pump 83 to an artery 300 (e.g. the femoral artery) of the patient. In this case, blood is suctioned from the artery 300 and is led into the reservoir 81, if appropriate via an air trap and/or defoamer 84 and a blood filter 85. Means 30 for regulating the flow of fluid are provided on the admission line 61. This flow regulator 30 has, in particular, a shut-off valve 34 with the aid of which the connection between reservoir 81 and vein 200 can be completely interrupted. In a particularly simple embodiment of the flow regulator, the admission line 61 is designed as an elastically yielding tubing in the area of the regulator, and the flow regulator 30 has a clamping member 31 which acts on this tubing and which is activated via an electric motor, preferably a stepping motor 32. The retroinfused flow of fluid is regulated by means of greater or lesser squeezing of the tubing line. The intravenous pressure in the vein 200 serves as a measure of the flow of fluid to be infused. For this purpose, the retroinfusion catheter 60 has a measurement line 63 which creates a communication between the inside of the vein and a pressure sensor 51 arranged at the distal end of the measurement line 63. However, the pressure sensor can also be provided as a proximal pressure sensor at the vein end 66 of the tubing line 60. A three-lumen catheter can also be used in this case, and the electrical connection of the pressure sensor to the means for measuring the venous pressure 50 can be guided through one of the other lumina of the catheter.

The intravenous pressure values thus measured are regulated by a control unit 10 which accordingly adjusts the clamping member via the stepping motor 32 of the flow regulator 30. An ultrasound measurement head 35 can additionally be provided on the admission line 61, which measurement head 35 is used, on the one hand, for detecting air bubbles in the fluid to be retroinfused, and, on the other hand, for determining the flow of fluid itself For this purpose, the ultrasound measurement head 35 has an ultrasound transmitter and an ultrasound receiver, the reflected ultrasound signal being used for detecting air bubbles and the Doppler-shifted ultrasound signal being used for determining the flow of fluid.

A further lumen of the catheter is a suction line 62 which is used for suctioning blood or retroinfusate from the vein 200 of the patient. The suction device 90 comprises a shut-off valve 91, a vacuum pump 92 and a container 93 for collecting the suctioned fluid. If appropriate, provision may be made for the suctioned fluid not to be collected and discarded, but for it to be returned cleaned to the patient. This is particularly useful in long-term applications of the device according to the invention: For this purpose, an intermediate reservoir 94 is provided, and the blood collected there is conveyed back to the patient into another vein 400 via a roller pump 95, an air trap 96 and, if appropriate, a blood filter.

For efficient retroinfusion, it is important that the vein 200 in which infusion is to be performed should be sealed off tightly upstream, as viewed in the infusion direction, so that the retroinfusate flows exclusively into the tissue area to be supplied. For this purpose, a pneumatically inflatable balloon is provided at the proximal end 66 of the catheter 60 as a sealing means 65. A fourth lumen of the catheter thus forms the control line 64 which does not open into the vein 200, but instead connects the balloon 65 to a pressure-controlled balloon pump 70. To control the pressure, a pressure sensor 71 is provided for the balloon pressure on the line 64. If the catheter is introduced into the vein in which retroinfusion is to be performed, the balloon 65 can be inflated by pumping in air, but also, if appropriate, by pumping in a liquid. It then closes off the vein tightly at the proximal end of the tubing line 60, while at the same time, however, the communication from admission line 61, suction line 62 and pressure-measurement line 63 to the inside of the vein 200 remains assured.

Figure 2:
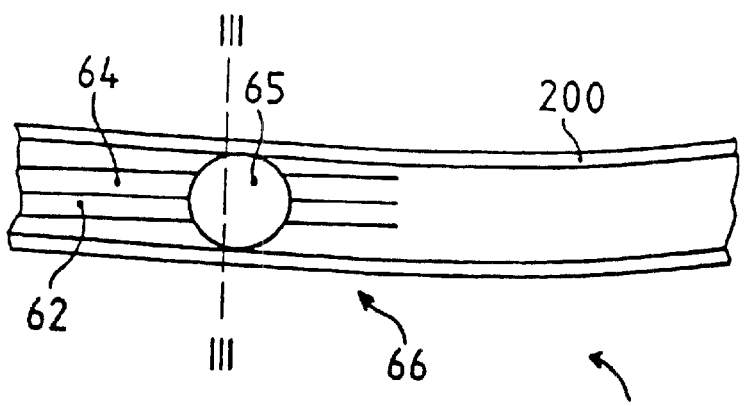
FIG. 2 shows a preferred embodiment of the vein end of the retroinfusion line of the device according to the invention, the line in the present case being designed as a four-lumen balloon catheter.

FIG. 2 shows, on an enlarged scale, the proximal end (introduced into the vein) of the retroinfusion catheter 60 of the retroinfusion device 100 shown in FIG. 1. The individual lines 62, 64 of the four-lumen catheter 60 (lines 61, 63 are not visible in the sectional view of FIG. 2) are welded together in that section of the catheter which can be introduced into the patient, and they separate into individual lines only to the outside of the patient. In this case, for example, the admission line 61 need not be a continuous line, and instead it can be connected, outside the patient, and via a coupling piece which is not shown, to a further line leading to the supply reservoir 61.

Figure 3:
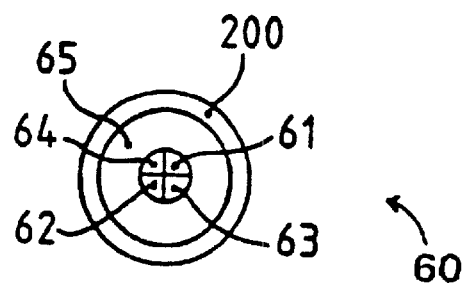
FIG. 3 shows a cross-section along the line III—III of the catheter in FIG. 2.

FIG. 3 shows a cross-section along the line III—III of the proximal end of the catheter in FIG. 2. The balloon 65 is in this case represented in the inflated state and tightly closes off the area between line 60 and vein 200. A three-lumen catheter with inflated balloon 65 is shown in the cross-section in FIG. 3A/

Figure 4:
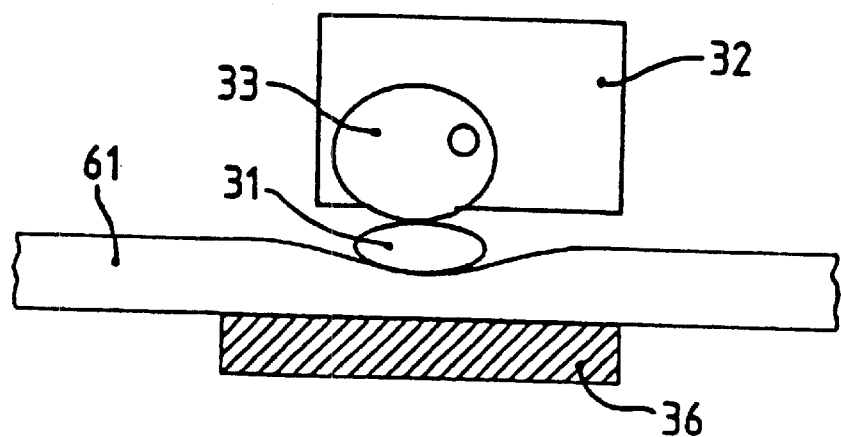
FIG. 4 shows a detail of a preferred embodiment of the flow regulator of the device in FIG. 1.

FIG. 4 shows an enlarged detail of a preferred embodiment of the flow regulator of the device in FIG. 1. In this area, the admission line 61 consists of an elastic tubing and is pressed together by a clamping member 31 designed as a crossbar. The crossbar is activated by a stepping motor 32, on whose axle an eccentric control cam 33 is provided, which acts on the crossbar. The clock frequency of the stepping motor is in this case chosen such that a new flow of fluid can be adjusted in the admission:line 61 in less than 25 ms. The corresponding control is effected via the control unit 10 which calculates the required setting of the clamping member from the respectively measured pressure and in particular from the instantaneous pressure pattern and sends corresponding instructions to the stepping motor. The line 61 in this case rests on a support 36 which prevents the line from moving during squeezing.

Figure 5:
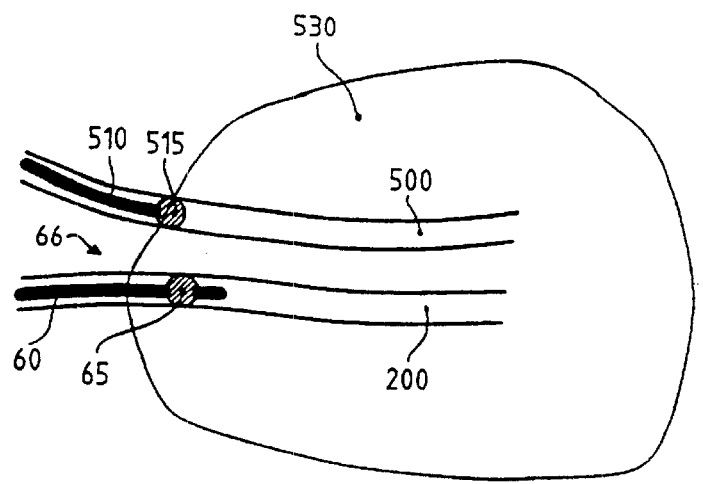
FIG. 5 shows the schematic representation of an application of the present. invention in myocardial protection during angioplasty;.

FIG. 5 is a schematic representation of a typical application of the present invention. This is when it is used for myocardial protection during an angioplasty procedure. Here, a coronary artery 500 which has been narrowed by arteriosclerotic plaque is widened by means of a balloon catheter 510. As long as the balloon 515 of the balloon catheter is inflated, the area of the myocardium 530 normally supplied by this artery is no longer supplied with sufficient oxygen and nutrients. For this purpose, a retroinfusion catheter 60 of the device according to the invention is introduced, with radiographic monitoring, into a vein 200 draining this area of the myocardium. Blood containing oxygen and nutrients, which has been taken from another of the patient's arteries, is retroinfused through the line 60 into the ischaemic area, so that functional impairment of this area is prevented (reference numeral 65 denotes the balloon of retroinfusion catheter 60).

To implement the method according to the invention in myocardial protection, the patient's vein in which retroinfusion is to be performed is selected depending on the area of the myocardium concerned, and the retroinfusion catheter 60 of the device 100 according to the invention is advanced, preferably with radiographic monitoring, into the vicinity of the area of the myocardium which is to be protected. Depending on whether venous blood flow is present or not, the intravenous pressure is determined, or an amount of fluid increasing with each pumping interval is infused and the plateau pressure thus set up is measured. The desired set value of the intravenous pressure can be determined from this during the retroinfusion interval. The set value preferably corresponds to the desired plateau pressure, but it may also be chosen to be slightly higher or lower.

Figure 6:
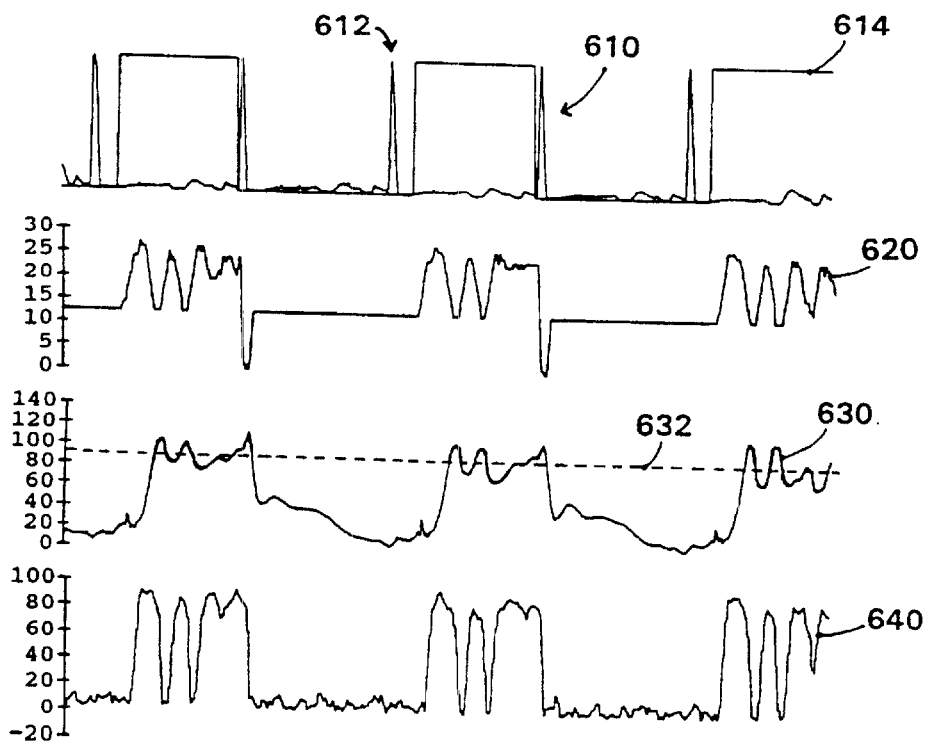
FIG. 6 shows diagrams of the time course of defined system parameters in implementing the method according to the invention.

In the method according to the invention, the retroinfusion with blood or another fluid is synchronized with the patient's heartbeat. To this end, for example, an electrocardiogram is taken using an ECG unit 20 (see FIG. 1), FIG. 6 shows the time course for some important system parameters while carrying out the method according to the invention. The control unit 10 evaluates the R waves 612 of the ECG lead 610. The retroinfusion and suction cycles are synchronized with this R wave of the heart cycle. The line 614 shows the trigger phase for the retroinfusion of fluid. This phase preferably begins after 15 to 50% of an R—R interval. The line 620 shows the momentary setting of the flow regulator, with changes upwards indicating an increase in flow, and with changes downwards indicating a decrease in flow. The curve 630 shows the actual pressure in the vein in which retrofusion is to be performed, the horizontal line 632 representing the preselected set pressure. The unit of pressure here is mmHg.

The line 640 shows the retroinfused fluid volume in ml/min. As is shown in the drawing, it is possible, with the method according to the invention, to maintain in the desired intravenous set pressure satisfactorily.

Blood or retroinfusate is suctioned from the vein 200 between the trigger phases.

Typically, about 0.5 to 1.5 ml of fluid are infused per pumping interval. The mean pumping quantity thus lies between 30 and 150 ml/min. However, these values are influenced by the catheter volume used, the catheter length and the preliminary pressure in the delivery-side high-pressure system.

Depending on the patient and on the retroinfused vein, typical retroinfusion pressures (set values) lie between 30 and 110 mmHg.

What is claimed is:

1. Method for the selective perfusion of fluids through blood vessels, controlled by the pressure in said blood vessels, comprising:
   introducing a tubing line into a patient's vein in which perfusion is to be performed, said tubing line being open at its proximal end for perfusing fluids through a tissue region,
   sealing off said vein from the line in the area of its proximal end,
   performing the following steps while maintaining said vein in the sealed-off condition:
   (1) pumping said fluid periodically at intervals into said vein via said tubing line and suctioning blood from said vein via said tubing line, said pumping and suctioning intervals being synchronized with the patient's heartbeat,
   (2) measuring the internal pressure of said vein, and
   (3) regulating said perfused flow of fluid during pumping in step (1) in such a way that a predefined set value for the internal pressure of said vein is maintained as closely as possible.

2. Method according to claim 1, wherein said infused fluid is an oxygen carrier.

3. Method according to claim 2 wherein said oxygen carrier comprises blood or a blood substitute.

4. Method according to claim 3, further comprising the step of withdrawing arterial blood from said patient, cleaning said blood and freeing said blood of air bubbles and reintroducing said blood into said vessel.

5. Method according to claim 1, wherein said predefined set value for the internal pressure of said vein is determined with said vein being sealed off and in the absence of venous blood flow, and by performing the steps of infusing fluid while increasing the flow of fluid at each pumping interval, measuring the internal pressure of the vein, and selecting a plateau pressure being created in said vein as said predefined set value.

6. Method according to claim 1, wherein said set value for the internal pressure of said vein is determined with said vein being sealed off and in the presence of venous blood flow, and by performing the steps of measuring the internal pressure of the vein, selecting a plateau pressure of the peak venous pressures being created in said vein in this process as said set value.

7. Method according to claim 1, wherein said fluid contains substances selected from the group of substances consisting of therapeutic and diagnostic active substances.

8. Method according to claim 6, further comprising the step of defoaming said blood which has been suctioned and, if appropriate, freeing said blood of air bubbles and returning said blood to said patient via another vein.

9. Device for the selective perfusion of a fluid through blood vessels, controlled by the pressure in said blood vessels, comprising:
   a tubing line which can be introduced into a patient's vein, said tubing line open at its proximal end thereof and being chargeable with a fluid under pressure which is to be pumped into said vein, said proximal end of said tubing line being provided with an enlargeable sealing means for sealing said vein off from said tubing line,
   a suction device connected to said tubing line for withdrawing blood from said vein of said patient, said control unit receiving signals from the patient's heartbeat and defining pumping and suction intervals which are synchronized with the patient's heart cycle,
   a control unit,
   means for measuring the internal pressure of said vein, said measuring means being connected to said control unit,
   means for regulating the perfused flow of fluid, said regulation means being operated by said control unit during a period when said enlargeable sealing means seals off said vein such that a defined set value for the internal pressure of the vein is maintained as constant as possible during pumping of said fluid.

10. Device according to claim 9 wherein said means for regulating the perfused flow of fluid comprise a flow regulator cooperating with said tubing line.

11. Device according to claim 10, wherein said tubing line is formed by an elastically yielding tubing in the area of said flow regulator, said flow regulator comprising a clamping member which is driven by an electric motor in order to press said elastic tubing together to a greater or lesser extent thereby controlling the flow of said fluid into said blood vessel.

12. Device according to claim 9, wherein a distal end of said tubing line is connected to a pressurized fluid reservoir having a pressure sensor for monitoring the pressure in said reservoir.

13. Device according to claim 12, further comprising a roller pump for feeding blood taken from an artery of said patient to said reservoir.

14. The device according to claim 9 wherein said tubing line comprises a multi-lumen lumen catheter, in particular an at least four-lumen catheter for retroinfusion, said multi-lumen lumen catheter comprising an admission line for said fluid, a suction line for suctioned blood, a measurement line for determining the internal pressure of a catheterised vein, and a control line for said enlargeable sealing means.

15. Device according to claim 14 wherein said measurement line communicates at one end with the inside of said vessel and has a pressure sensor arranged at its other end.

16. Device according to claim 9, wherein said sealing means comprises a pressure-controlled, inflatable balloon.

17. Device according to claim 9, wherein said means for measuring said internal pressure of said blood vessel comprises a pressure sensor arranged at the proximal end of said tubing line, said pressure sensor connected to said control unit.

18. Device according to claim 9, wherein said suction device comprises a vacuum pump and a container for suctioned blood.

19. Device according to claim 9, further comprising a reservoir, a roller pump and an air trap being connected to one another and being further connected to said suction device, for withdrawing blood from said patient, cleaning said suctioned blood and delivering said cleaned blood to a vein of said patient.

20. Method for the selective perfusion of fluids through blood vessels, controlled by the pressure in said blood vessels, comprising:
   introducing a tubing line into a patient's vein in which perfusion is to be performed, said tubing line being open at its proximal end for perfusing fluids through a tissue region,
   sealing off said vein from the line in the area of its proximal end,
   performing the following steps while maintaining said vein in the sealed-off condition:
      (1) pumping said fluid periodically at intervals into said vein via said tubing line, the pumping intervals being synchronized with the patient's heartbeat,
      (2) measuring the internal pressure of said vein, and
      (3) regulating said perfused flow of fluid during pumping in step (1) in such a way that a predefined set value for the internal pressure of said vein is maintained as closely as possible,
   said predefined set value for the internal pressure of said vein being determined with said vein being sealed off and in the absence of venous blood flow, and by performing the steps of infusing fluid while increasing the flow of fluid at each pumping interval, measuring the internal pressure of the vein, and selecting a plateau pressure being created in said vein as said predefined set value.

21. Method for the selective perfusion of fluids through blood vessels, controlled by the pressure in said blood vessels, comprising:
   introducing a tubing line into a patient's vein in which perfusion is to be performed, said tubing line being open at its proximal end for perfusing fluids through a tissue region,
   sealing off said vein from the line in the area of its proximal end,
   performing the following steps while maintaining said vein in the sealed-off condition:

(1) pumping said fluid periodically at intervals into said vein via said tubing line, the pumping intervals being synchronized with the patient's heartbeat,
(2) measuring the internal pressure of said vein, and
(3) regulating said perfused flow of fluid during pumping in step (1) in such a way that a predefined set value for the internal pressure of said vein is maintained as closely as possible, said predefined set value for the internal pressure of said vein being determined with said vein being sealed off and in the presence of venous blood flow, and by performing the steps of measuring the internal pressure of the vein, selecting a plateau pressure of the peak venous pressures being created in said vein in this process as said set value.

22. The method according to claim 20, or claim 21, further comprising the steps of infusing said fluid into said vein periodically via said tubing line, and suctioning blood from said vein via said tubing line.

23. The method according to claim 22 wherein said pumping and suction steps are performed in intervals that are synchronized with the patient's heartbeat.

24. Device for the selective perfusion of a fluid through blood vessels, controlled by the pressure in said blood vessels, comprising:

a tubing line which can be introduced into a patient's vein, said tubing line open at its proximal end thereof and being chargeable with a fluid under pressure which is to be pumped into said vein, said proximal end of said tubing line being provided with an enlargeable sealing means for sealing said vein off from said tubing line, said tubing line comprising a multi-lumen catheter, in particular an at least three-lumen artery catheter for perfusion, said multi-lumen catheter comprising an admission line for said fluid, a measurement line for determining the internal pressure of a catheterised artery, and a control line for said enlargeable sealing means, a control unit, means for measuring the internal pressure of said vein, said measuring means being connected to said control unit, means for regulating the perfused flow of fluid, said regulation means being operated by said control unit during a period when said enlargeable sealing means seals off said vein such that a defined set value for the internal pressure of the vein is maintained as constant as possible during pumping of said fluid.

25. Device according to claim 24, wherein said vessel comprises a vein and wherein said device further comprises a suction device connected to said tubing line for withdrawing blood from said vein of said patient, said control unit receiving signals from the patient's heartbeat and defining pumping and suction intervals which are synchronized with the patient's heart cycle.

26. The device according to claim 25, wherein said multi-lumen catheter is an at least four-lumen catheter for retroinfusion further comprising a suction line for suctioned blood.

* * * * *